(12) United States Patent
Kristensen et al.

(10) Patent No.: US 10,001,490 B2
(45) Date of Patent: Jun. 19, 2018

(54) BIOCHEMICAL MARKERS FOR PULMONARY AND OTHER DISEASES

(71) Applicant: NORDIC BIOSCIENCE A/S, Herlev (DK)

(72) Inventors: Jacob Hull Kristensen, Soborg (DK); Diana Julie Oersnes-Leeming, Espergaerde (DK); Morten Karsdal, Kobenhavn O (DK)

(73) Assignee: Nordic Bioscience A/S, Herlev (DK)

( * ) Notice: Subject to any disclaimer, the term of this patent is extended or adjusted under 35 U.S.C. 154(b) by 0 days. days.

(21) Appl. No.: 15/111,062

(22) PCT Filed: Jan. 8, 2015

(86) PCT No.: PCT/EP2015/050269
§ 371 (c)(1),
(2) Date: Jul. 12, 2016

(87) PCT Pub. No.: WO2015/104342
PCT Pub. Date: Jul. 16, 2015

(65) Prior Publication Data
US 2016/0334416 A1 Nov. 17, 2016

(30) Foreign Application Priority Data
Jan. 13, 2014 (GB) .................................. 1400472.5

(51) Int. Cl.
| | |
|---|---|
| *G01N 33/53* | (2006.01) |
| *G01N 33/68* | (2006.01) |
| *C07K 16/18* | (2006.01) |
| *C07K 16/40* | (2006.01) |
| *G01N 33/577* | (2006.01) |

(52) U.S. Cl.
CPC ......... *G01N 33/6878* (2013.01); *C07K 16/18* (2013.01); *C07K 16/40* (2013.01); *G01N 33/577* (2013.01); *G01N 33/6893* (2013.01); *C07K 2317/33* (2013.01); *C07K 2317/34* (2013.01); *G01N 2333/78* (2013.01); *G01N 2333/96411* (2013.01); *G01N 2333/96419* (2013.01); *G01N 2800/122* (2013.01); *G01N 2800/7052* (2013.01)

(58) Field of Classification Search
None
See application file for complete search history.

(56) References Cited

U.S. PATENT DOCUMENTS

| | | | |
|---|---|---|---|
| 8,101,717 B2 * | 1/2012 | Weiss ........................ | A61K 8/64 530/353 |
| 9,068,942 B2 * | 6/2015 | Turino ............... | G01N 30/7233 |
| 2013/0273586 A1 | 10/2013 | Turino et al. | |

FOREIGN PATENT DOCUMENTS

| | | |
|---|---|---|
| WO | 2009059972 A2 | 5/2009 |
| WO | 2010115749 A2 | 10/2010 |

OTHER PUBLICATIONS

Campbell (from Monoclonal Antibody Technology, Elsevier Sci Pub. 1984, total 16 pages).*
Barroso, B., Abello, N., & Bischoff, R. 2006, "Study of human lung elastin degradation by different elastases using high-performance liquid chromatography/mass spectrometry", Anal.Biochem., vol. 358, No. 2, pp. 216-224.
Carter, R. I., Mumford, R. A., Treonze, K. M., Finke, P. E., Davies, P., Si, Q., Humes, J. L., Dirksen, A., Piitulainen, E., Ahmad, A., & Stockley, R. A. 2011, "The fibrinogen cleavage product Aalpha-Val360, a specific marker of neutrophil elastase activity in vivo", Thorax, vol. 66, No. 8, pp. 686-691.
Carter, R. I., Ungurs, M. J., Mumford, R. A., & Stockley, R. A. 2013, "Aalpha-Val360: a marker of neutrophil elastase and COPD disease activity", Eur.Respir.J., vol. 41, No. 1, pp. 31-38.
Finlay, G. A., O'Driscoll, L. R., Russell, K. J., D'Arcy, E. M., Masterson, J. B., Fitzgerald, M. X., & O'Connor, C. M. 1997, "Matrix metalloproteinase expression and production by alveolar macrophages in emphysema", Am.J.Respir.Crit Care Med., vol. 156, No. 1, pp. 240-247.
Gefter, M. L., Margulies, D. H., & Scharff, M. D. 1977, "A simple method for polyethylene glycol-promoted hybridization of mouse myeloma cells", Somatic.Cell Genet., vol. 3, No. 2, pp. 231-236.
He, J., Turino, G. M., & Lin, Y. Y. 2010, "Characterization of peptide fragments from lung elastin degradation in chronic obstructive pulmonary disease", Exp.Lung Res., vol. 36, No. 9, pp. 548-557.
Heinz, A., Taddese, S., Sippl, W., Neubert, R. H., & Schmelzer, C. E. 2011, "Insights into the degradation of human elastin by matrilysin-1", Biochimie, vol. 93, No. 2, pp. 187-194.
Ma, S., Lin, Y. Y., & Turino, G. M. 2007, "Measurements of desmosine and isodesmosine by mass spectrometry in COPD", Chest, vol. 131, No. 5, pp. 1363-1371.
Maclay, J. D., McAllister, D. A., Rabinovich, R., Haq, I., Maxwell, S., Hartland, S., Connell, M., Murchison, J. T., van Beek, E. J., Gray, R. D., Mills, N. L., & Macnee, W. 2012, "Systemic elastin degradation in chronic obstructive pulmonary disease", Thorax, vol. 67, No. 7, pp. 606-612.
Rosas, I. O., Richards, T. J., Konishi, K., Zhang, Y., Gibson, K., Lokshin, A. E., Lindell, K. O., Cisneros, J., Macdonald, S. D., Pardo, A., Sciurba, F., Dauber, J., Selman, M., Gochuico, B. R., & Kaminski, N. 2008, "MMP1 and MMP7 as potential peripheral blood biomarkers in idiopathic pulmonary fibrosis", PLoS.Med., vol. 5, No. 4, p. e93.

(Continued)

*Primary Examiner* — Changhwa J Cheu
(74) *Attorney, Agent, or Firm* — Benjamin Aaron Adler

(57) ABSTRACT

Provided is a method of bioassay for the quantification of peptide fragments elevated in lung diseases such as COPD, SCC, or IPF. The peptide fragments comprise a neo-epitope formed at a cleavage site by cleavage in vivo of elastin by a proteinase. In the method a sample is contacted with an antibody having specific binding affinity for the neo-epitope amino acid sequence and determining the level of binding is determined where the antibody binds one of the following terminal sequences: . . . FGPGVV, . . . VPGLGV or IKAPKL . . . . Also provided are antibodies and immunoassay kits for use in such methods.

7 Claims, 8 Drawing Sheets

(56) References Cited

OTHER PUBLICATIONS

Skjot-Arkil, H., Clausen, R. E., Nguyen, Q. H., Wang, Y., Zheng, Q., Martinez, F. J., Hogaboam, C. M., Han, M., Klickstein, L. B., Larsen, M. R., Nawrocki, A., Leeming, D. J., & Karsdal, M. A. 2012, "Measurement of MMP-9 and -12 degraded elastin (ELM) provides unique information on lung tissue degradation", BMC. Pulm.Med., vol. 12, No. 1, p. 34.

Skjot-Arkil, H., Clausen, R. E., Rasmussen, L. M., Wang, W., Wang, Y., Zheng, Q., Mickley, H., Saaby, L., Diederichsen, A. C., Lambrechtsen, J., Martinez, F. J., Hogaboam, C. M., Han, M., Larsen, M. R., Nawrocki, A., Vainer, B., Krustrup, D., Bjorling-Poulsen, M., Karsdal, M. A., & Leeming, D. J. 2013, "Acute Myocardial Infarction and Pulmonary Diseases Result in Two Different Degradation Profiles of Elastin as Quantified by Two Novel ELISAs", PLoS.One., vol. 8, No. 6, p. e60936.

Starcher, B., O'Neal, P., Granstein, R. D., & Beissert, S. 1996, "Inhibition of neutrophil elastase suppresses the development of skin tumors in hairless mice", J.Invest Dermatol., vol. 107, No. 2, pp. 159-163.

Zhang, J., Jin, X., Fang, S., Wang, R., Li, Y., Wang, N., Guo, W., Wang, Y., Wen, D., Wei, L., Dong, Z., & Kuang, G. 2005, "The functional polymorphism in the matrix metalloproteinase-7 promoter increases susceptibility to esophageal squamous cell carcinoma, gastric cardiac adenocarcinoma and non-small cell lung carcinoma", Carcinogenesis, vol. 26, No. 10, pp. 1748-1753.

Skjot-Arkil, H. et al., "Macrophage mediated proteolytic remodelling of the extracellular matrix in atherosclerosis results in neoepitopes: a potential new class of biomarkers", Assay and drug development technologies, Oct. 2010, 542-552.

\* cited by examiner

BIOCHEMICAL MARKERS FOR PULMONARY AND OTHER DISEASES

The present invention relates to immunological methods and materials for the detection or quantitation of fragments of elastin.

Elastin is an essential protein for the structure and function of the extracellular matrix. The amino acid sequence of human elastin is SEQ ID NO:1. It provides resilience and elasticity to many organs and tissues. These include the lung, skin, aorta, ligaments, tendons and cartilage. Elastin is formed from a precursor tropoelastin and involves cross-links formed by pyridinium, desmosine and isodesmosine structures. Although elastin is highly stable, the matrix metalloproteinases (MMPs) and serine proteases such as human neutrophil elastase (HNE) are able to degrade elastin fibres, followed by a loss in elasticity and function. In the lungs this loss in elasticity can lead to pathological features such as chronic obstructive pulmonary disease (COPD) with co-existing emphysema (Maclay et al. 2012). Furthermore "vast" deposition of elastin derived peptides in the lung can lead to interstitial diseases such as idiopathic pulmonary fibrosis (IPF). Studies have shown that certain elastin derived fragments are upregulated in serum from patients suffering from pulmonary fibrotic disorders (Skjot-Arkil et al. 2012).

Surprisingly, we have been able to identify certain HNE- or MMP7-derived fragments of elastin, which can serve as reliable biomarkers for diagnosis and prognosis of various pulmonary diseases.

An ELISA against elastin degraded by other MMPs has been described (Skjot-Arkil, Clausen, Nguyen, Wang, Zheng, Martinez, Hogaboam, Han, Klickstein, Larsen, Nawrocki, Leeming, & Karsdal 2012; Skjot-Arkil et al. 2013). This utilises a monoclonal antibody targeting a fragment of elastin that is derived by cleavage by MMP9 and MMP12. This assay is also applied towards pulmonary disorders. Biomarkers described herein are different as they are based on selected elastin fragments that are derived by HNE and/or MMP7. These are more specific towards lung disorders (Finlay et al. 1997; Rosas et al. 2008; Starcher et al. 1996; Zhang et al. 2005) compared to the MMP9 and MMP12 proteases.

ELISA kits that quantify intact MMP7 and HNE are known but these only measure the concentration of the proteases and not their effect on a target molecule, i.e. their generation of neo-epitopes in elastin.

ELISA kits quantifying intact elastin are also available. This is different from the present invention, which does not detecting intact elastin but rather neo-epitopes generated during degradation of elastin.

Many HNE derived elastin fragments have been detected by mass spectrometry of digested elastin, see for instance He, Turino, & Lin 2010 where a few of these are also detected and quantitated in plasma and/or sputum. However these detected and quantitated peptides are different from the fragments used in the present invention.

Matured elastin (desmosine cross-link) in COPD patients has been quantified by mass spectrometry (Ma, Lin, & Turino 2007). They only quantified the production of intact elastin and not protease derived fragments.

Cleavage sites of elastin with various proteases are already determined and published. This also includes HNE (Barroso, Abello, & Bischoff 2006; He, Turino, & Lin 2010a) and MMP7 (Heinz et al. 2011) cleaved elastin. However, these disclosures do not describe detection of elastin fragments using antibodies being specific for neo-epitopes generated during proteolytic degradation of elastin. Neither do they disclose which fragments of elastin formed in vitro have diagnostic relevance or are formed in vivo or can even be detected in biological fluid samples.

The present invention now provides a method of bioassay for the quantification of peptide fragments comprising a neo-epitope formed at a cleavage site by cleavage in vivo of elastin by a proteinase at said site, said method comprising contacting a sample comprising said peptide fragments with an immunological binding partner having specific binding affinity for a said neo-epitope and determining the level of binding of said immunological binding partner to peptide fragments in said sample, wherein said immunological binding partner has specific binding affinity for one of the following terminal sequences:

```
                                        (SEQ ID NO: 2)
        .........FGPGVV||'334

(SEQ ID NO: 3)
        .........VPGLGV||'602

(SEQ ID NO: 4)
        208'||IKAPKL......
```

The symbol ‖ indicates cleavage of the elastin sequence between the numbered point of SEQ ID NO:1 and the next amino acid in the case of C-terminal cleavage fragments and the preceding amino acid in the case of an N-terminal cleavage.

The immunological binding partner is preferably not specifically reactive with the sequence . . . FGPGVVG (SEQ ID NO:5) if it is reactive with . . . FGPGVV, and is not specifically reactive with . . . VPGLGVG (SEQ ID NO:6) if it is reactive with . . . VPGLGV, and is not specifically reactive with PIKAPKL . . . (SEQ ID NO:7) if it is reactive with IKAPKL . . . . Preferably, the immunological binding partner is also not specifically reactive with peptides further extended with the relevant part of the elastin amino acid sequence beyond the cleavage site.

Said immunological binding partner may be a monoclonal antibody or a fragment of a monoclonal antibody having specific binding affinity.

The invention includes an immunological binding partner specifically reactive with one of the following terminal sequences derived from elastin:

```
        .........FGPGVV||'334

.........VPGLGV||'602

208'||IKAPKL......
```

Preferably, the immunological binding partner is not specifically reactive with the sequence . . . FGPGVVG if it is reactive with . . . FGPGVV, and is not specifically reactive with . . . VPGLGVG if it is reactive with . . . VPGLGV, and is not specifically reactive with PIKAPKL . . . if it is reactive with IKAPKL . . . .

The immunological binding partner may be a monoclonal antibody or a binding fragment thereof.

The invention includes an immunoassay kit comprising an immunological binding partner as described, and a competition agent which binds said immunological binding partner, and optionally one or more of a wash reagent, a buffer, a stopping reagent, an enzyme label, an enzyme label substrate, calibration standards, an anti-mouse antibody and instructions for conducting an assay using said kit.

The result of said assay may produce an index indicative of the degree of risk in a particular patient of the presence of COPD, IPF, or SCC or the extent or severity of such a condition. Patients having a value for said measurement above a threshold level may be recommended for further investigation or for the prescribing of medication for treatment thereof and such follow up investigations or treatment may form part of the method of the invention.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be a synthetic peptide or a purified native peptide formed by cleavage of elastin.

Alternatively, said method is conducted as a sandwich immunoassay in which said immunological binding partner and a further immunological binding partner having specific binding affinity for a peptide sequence contained in peptide fragments bound by said immunological binding partner are incubated in the presence of said sample and both bind together to said peptide fragments in the sample. One suitable method could be a competition immunoassay using monoclonal antibodies or antibody binding fragments binding to neo-epitopes of fragments of elastin.

Appropriately selected synthetic peptides coated onto the solid surface of a microtitre plate could compete with the sample for binding to the monoclonal antibodies or binding fragments. Alternatively, purified, native fragments from one or more of these proteins carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin.

In certain preferred methods, the sample is a patient derived sample, and the method further comprises comparing the determined level of said binding of said peptide fragments with values characteristic of (a) comparable healthy individuals and/or (b) a relevant pathological condition and optionally associating a higher level of the measured peptide (normally indicated by a higher level of binding) with a more severe degree of a said condition. The sample may be a sample of urine, serum, blood, plasma, or saliva, by way of example.

An aspect of the present invention relates to the development of monoclonal antibodies recognising neo-epitopes as described above. This can be achieved by immunising mice with synthetic peptides originating from the amino acid sequence of elastin (particularly the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-terminal prolongated form of the immunising peptide (for a C-terminal neo-epitope) or an N-terminal prolongated form of the immunising peptide (for an N-terminal neo-epitope). Antibodies for neo-epitopes may also be evaluated to establish a lack of binding capacity to intact elastin. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of elastin by a protease at an end-site in any one of the partial sequences set out above, and may be for instance a monoclonal antibody or a binding fragment thereof.

The invention includes a cell line producing a monoclonal antibody against a C-terminal or N-terminal neo-epitope formed by cleavage of elastin at the end-sites of sequences in any one of the partial sequences set out above.

The invention further provides a peptide comprising a C-terminal or N-terminal neo-epitope formed by cleavage of elastin in any one of the partial sequences set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of elastin in any one of the partial sequences set out above.

The invention further comprises a vector comprising a nucleic acid sequence comprising an expression signal and a coding sequence which codes for the expression of a peptide comprising a C-terminal or N-terminal neo-epitope formed by cleavage of elastin in any one of the partial sequences set out above and further includes a host cell transformed with such a vector and expressing a said peptide.

Yet another aspect of the invention relates to kits, which can be used conveniently for carrying out the methods described above. Such kits may include (1) a microtitre plate coated with synthetic peptide carrying the sequence of the neo-epitope; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native protein fragments; (2) a monoclonal antibody recognising a neo-epitope on fragments of any one of said proteins, and reactive with said purified fragments; and (3) a labelled anti-mouse IgG immunoglobulin. Alternatively, such kits may include (1) a microtitre plate coated with streptavidin; (2) a synthetic peptide linked to biotin, said synthetic peptide carrying the sequence of a neo-epitope; (3) a monoclonal antibody recognising a neo-epitope on said protein fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin, said peptide carrying the sequence of a neo-epitope; (3) a monoclonal antibody recognising a neo-epitope on said protein fragments (and reactive with said synthetic peptide) and conjugated to horseradish peroxidase. Yet another alternative could be a kit including (1) a microtitre plate coated (directly or indirectly) with a monoclonal antibody or a fragment thereof, said antibody recognising a neo-epitope on said protein fragment; (2) a HRP labelled synthetic peptide carrying the sequence of a neo-epitope, or alternatively, a kit including (1) a microtitre plate coated (directly or indirectly) with a monoclonal antibody or a fragment thereof, said antibody recognising a neo-epitope on said protein fragment; (2) a biotin-labelled synthetic peptide carrying the sequence of a neo-epitope; (3) HRP-labelled streptavidin.

Thus, the invention includes an immunoassay kit comprising an immunological binding partner as described herein, and a competition agent which binds said immunological binding partner, and optionally one or more of a wash reagent, a buffer, a stopping reagent, an enzyme label, an enzyme label substrate, calibration standards, an anti-mouse antibody and instructions for conducting a said immunoassay.

The assays described herein are useful in the diagnosis of the described diseases and elastin related pathologies in general in patients. In addition, the tests are useful for the assessment of disease progression, and the monitoring of response to therapy. The immunological binding partners of the invention may also be used in immunostaining to show the presence or location of cleavage products of elastin described herein.

The invention will be further described and illustrated with reference to the following examples illustrating the principles and practice of preferred embodiments. The Examples make reference to the results presented in the accompanying drawings in which.

Figure 6:
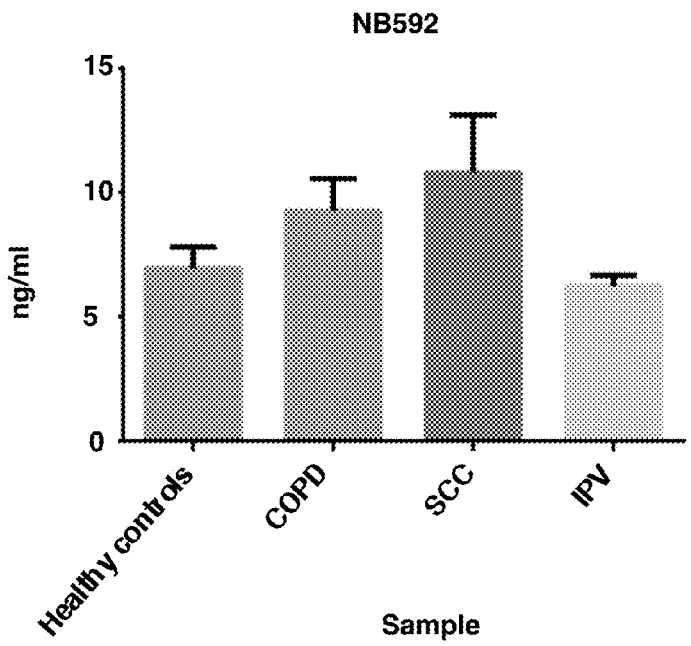

FIG. 6 shows concentrations of the NB592 free peptides in serum from COPD, IPF and squamous cell carcinoma (SCC) of patients as well as controls obtained in Example 4. The standard error of the mean is shown. Free peptide concentrations were applied as reference.

Figure 7:
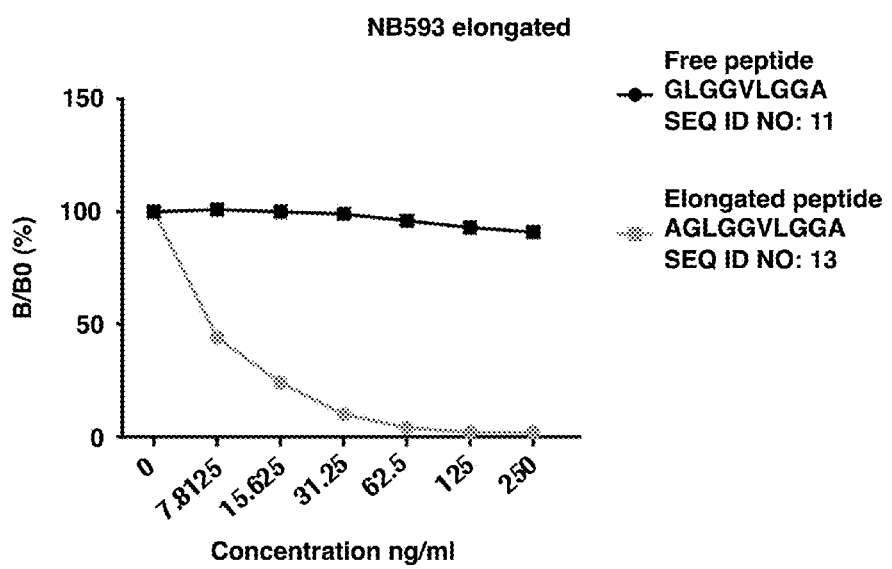

FIG. 7 shows results obtained in Example 5 of an ELISA and shows a measured B/B$_0$ ratio compared to the concentration of free peptide (NB593) (SEQ ID NO:11) and elongated peptide (AGLGGVLGGA, SEQ ID NO:13) after incubation with the NB593 monoclonal antibody. There is almost no reactivity towards the elongated peptide.

Figure 8:
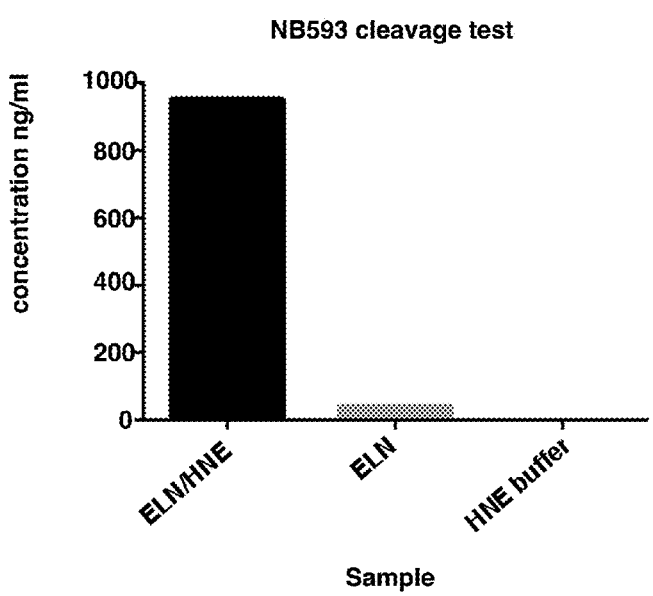

FIG. 8 shows results characterising the NB593 monoclonal antibody obtained in Example 5.

Figure 9:
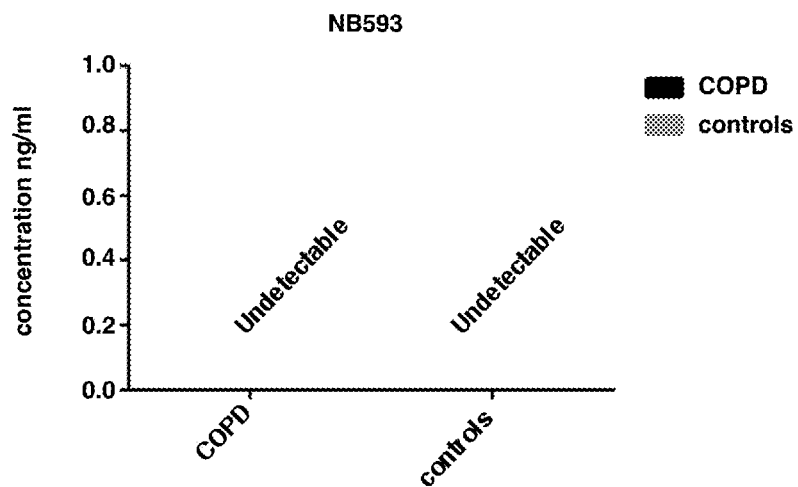

FIG. 9 shows the results of testing NB593 antibody on various disease samples from patients as well as healthy controls. The NB593 fragments were undetectable in serum.

Figure 10:
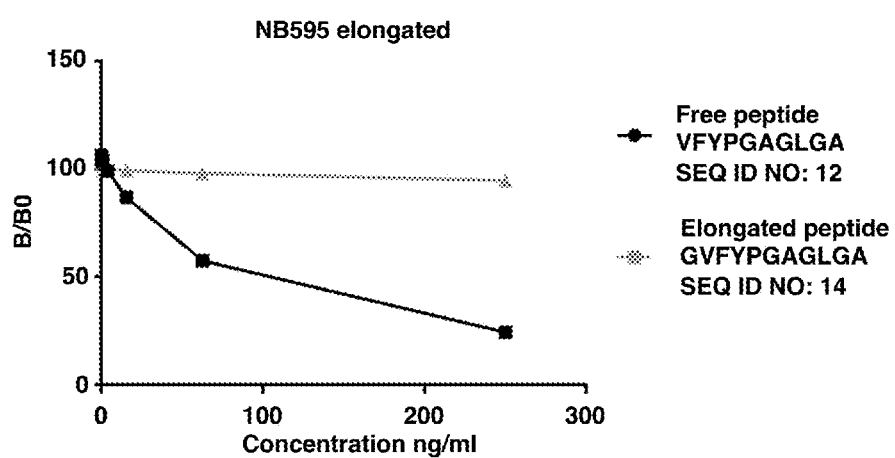

FIG. 10 shows the results of an ELISA conducted in Example 6 and shows the percent inhibition of the signal by free peptide (NB595) (SEQ ID NO:12) and elongated peptide (GVFYPGAGLGA, SEQ ID NO:14) of the NB595 monoclonal antibody. There is almost no inhibition by the elongated peptide.

Figure 11:
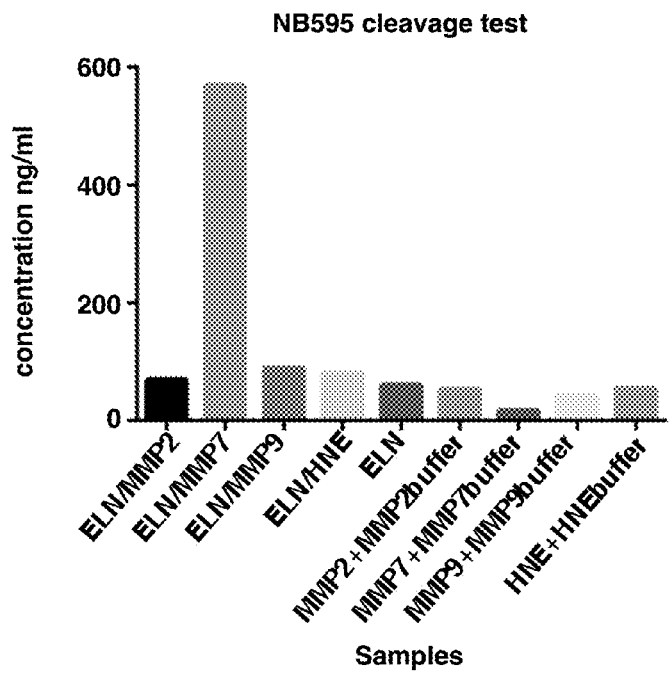

FIG. 11: shows results characterising the NB595 monoclonal antibody obtained in Example 6.

Figure 12:
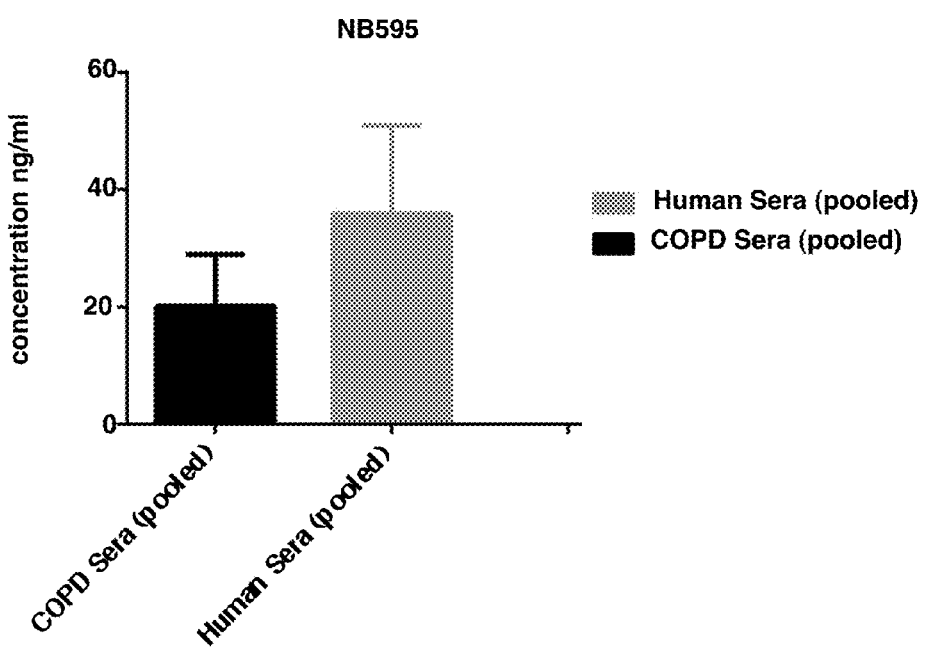

FIG. 12 shows concentrations of the NB595 fragments in serum from COPD patients and healthy controls. The NB595 fragment is not elevated in COPD.

Figure 13:
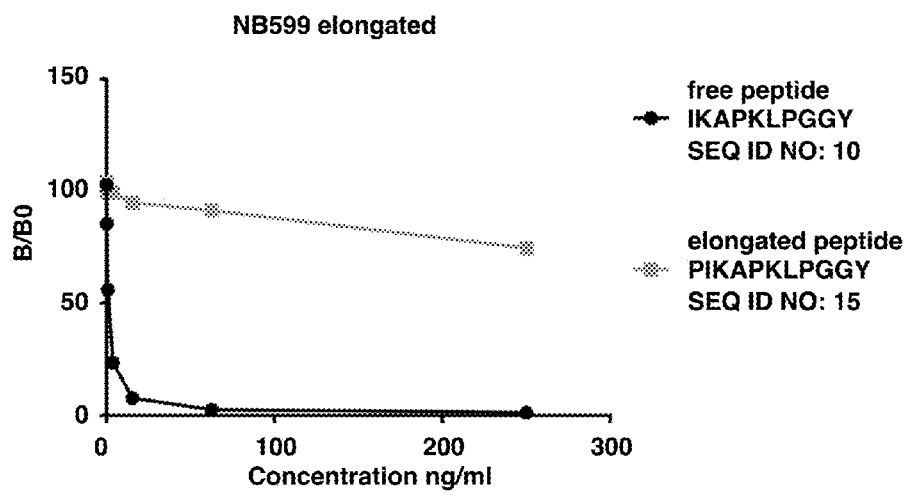

FIG. 13 shows the results of an ELISA conducted in Example 7 and shows the percent inhibition of signal by free peptide (NB599) (SEQ ID NO:10) and elongated peptide (PIKAPKLPGGY, SEQ ID NO:15) of the NB599 monoclonal antibody. There is a low reactivity with the antibody towards the elongated peptide compared to the free peptide.

Figure 14:
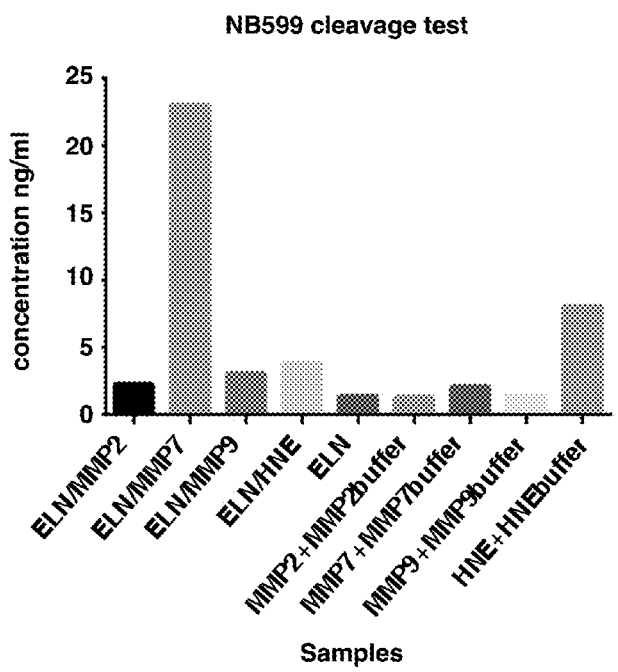

FIG. 14 shows results characterising the NB599 monoclonal antibody which were obtained in Example 7.

Figure 15:
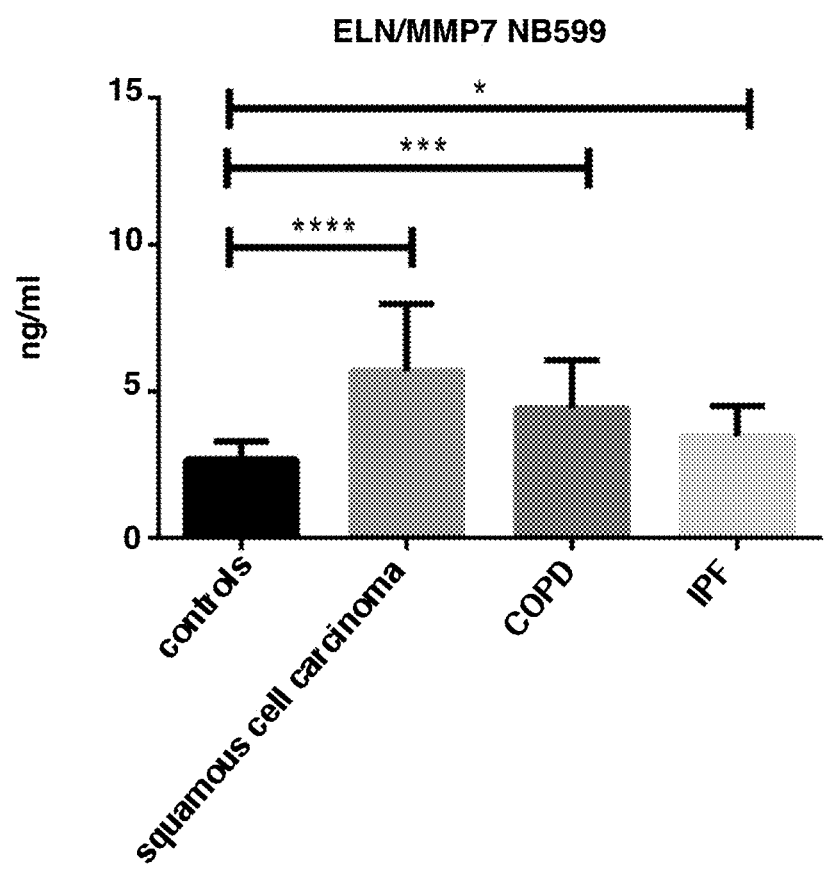

FIG. 15 shows the concentration of the NB599 elastin fragments in serum from controls, squamous cell carcinoma (SCC), COPD and IPF patients. There is a significant difference between control and SCC and between COPD and controls. There is also a statistical difference between IPF and control.

EXAMPLE 1

Selection of Peptides for Immunizations

The following peptides were selected for immunisation:

```
NB590: Amino Acid # (HNE derived)
                              (SEQ ID NO: 8)
325'GGPGFGPGVV||'334

NB592: Amino Acid # (HNE derived)
                              (SEQ ID NO: 9)
593'VGAGVPGLGV||'602

NB599: Amino Acid # (MMP7 derived)
                              (SEQ ID NO: 10)
208'||IKAPKLPGGY'217

NB593: Amino Acid # (HNE derived)
                              (SEQ ID NO: 11)
743'||GLGGVLGGA'752

NB595: Amino Acid # (MMP7 derived)
                              (SEQ ID NO: 12)
41'||VFYPGAGLGA'50
```

The cleavage sites involved are amongst those previously determined by others (He, Turino, & Lin 2010d; Heinz et al. 2011a). We chose the immunisation peptides as the first 10 amino acids either downstream or upstream of the cleavage sites.

EXAMPLE 2

Development of Monoclonal Antibodies

Six 4-6 week old Balb/C mice were immunized subcutaneously in the abdomen with 200 μL emulsified antigen (50 μg per immunization) using mentioned immunogen peptide conjugated to KLH at its N-terminus for C-terminal epitopes and at its C-terminus for N-terminal epitopes according to a standard procedure. Immunizations were continued until stable titer levels were obtained.

The mouse with the highest titer was selected for fusion and boosted intravenously with 50 μg immunogen in 100 μL 0.9% sodium chloride solution three days before isolation of the spleen for cell fusion.

The fusion procedure was followed by known procedures (Gefter, Margulies, & Scharff 1977). Supernatants were collected and monoclonal antibodies were purified using Protein G columns according to manufacturer's instructions (GE Healthcare Life Science).

Selection of Neo-Epitope Specific Monoclonal Antibodies:

Antibodies were selected upon their peptide-specificity using the homologous peptide used for immunisation (selection peptide) in non-conjugated form and de-selected against an elongated version of the peptide extended by one amino acid of the elastin sequence beyond the cleavage site thereby ensuring that only antibodies with a neo-epitope specificity was selected for further analysis.

Subsequently, the reactivity of the antibodies against intact, native and cleaved elastin was tested.

And finally, serum samples from healthy and diseased subjects were tested in the above mentioned assay protocol.

Assay Protocol:

A 96-well streptavidin plate was coated with screening peptide dissolved in coater buffer and incubated for 30 minutes at 20° C. After incubation, the plate was washed five times in washing buffer (20 mM Tris, 50 mM NaCl, pH 7.2). 20 μL of peptide (selection, de-selection or nonsense) or human sample were added in duplicate to appropriate wells, followed by 100 μL of POD-conjugated monoclonal antibody, and then the plate was incubated for 1 hour on a shaker. After washing, 100 μL tetramethylbenzidine (TMB) (Kem-En-Tec) was added and the plate was incubated for 15 minutes at 20° C. in the dark.

All the above incubation steps included shaking at 300 rpm.

The TMB reaction was stopped by adding 100 μL of stopping solution (1% $H_2SO_4$). Absorbance was measured at 450 nm with 650 nm as the reference. A master calibrator prepared from the selection peptide was used as a calibration curve and plotted using a 4-parametric mathematical fit model.

All serum samples were diluted 1:2 in incubation buffer prior to measurements.

EXAMPLE 3 MONOCLONAL ANTIBODY NB590

Figure 1:
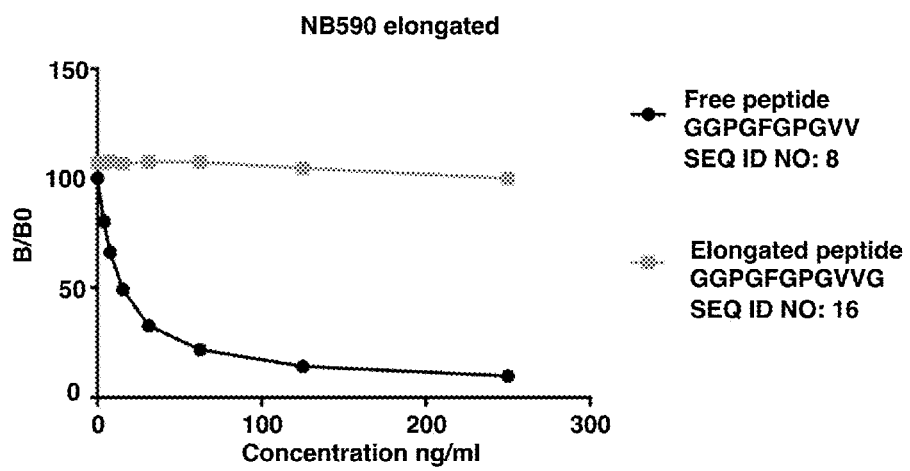
FIG. 1 shows results obtained in Example 3 of an ELISA and shows a measured B/B$_0$ ratio compared to the concentration of free peptide SEQ ID NO:8) and elongated peptide (NB590) (GGPGFGPGVVG, SEQ ID NO:16) after incubation with the NB590 monoclonal antibody. There is almost no reactivity towards the elongated peptide.

FIG. 1 shows the reactivity of the free and elongated peptide towards the NB590 antibody. A decrease in absorbance is seen together with an increase in free peptide concentration. This is due an increased reaction with the free peptide instead of the screening peptide in the wells. This was not the case for the elongated peptide as the stable $B/B_0$ levels indicated a very low or no reaction between the NB590-01 antibody and the elongated peptide.

Figure 2:
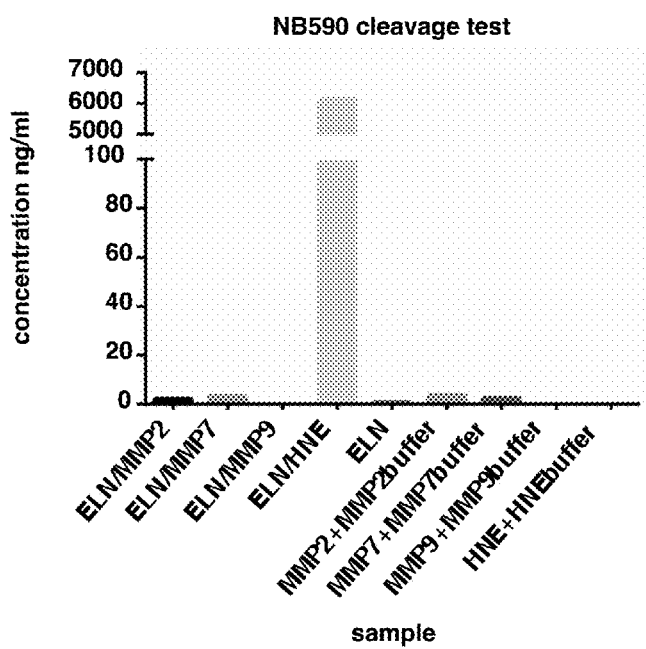
FIG. 2 shows results characterising the NB590 monoclonal antibody obtained in Example 3.

Subsequently, the NB590 antibody was tested towards elastin (ELN), elastin cleaved in vitro with MMP2, MMP7, MMP9 and HNE and the proteases in their respective buffers (FIG. 2). The reactivity of the selected proteases in their buffers only, is also included. The NB590 monoclonal antibody clearly measures the elastin fragments derived by HNE. Free peptide concentrations were applied as reference. The NB590 antibody has a very high reactivity towards elastin cleaved with HNE. The reactivity of the NB590 antibody and intact elastin or elastin cleaved with other proteases is close to the lower limit of detection of the assay.

Figure 3:
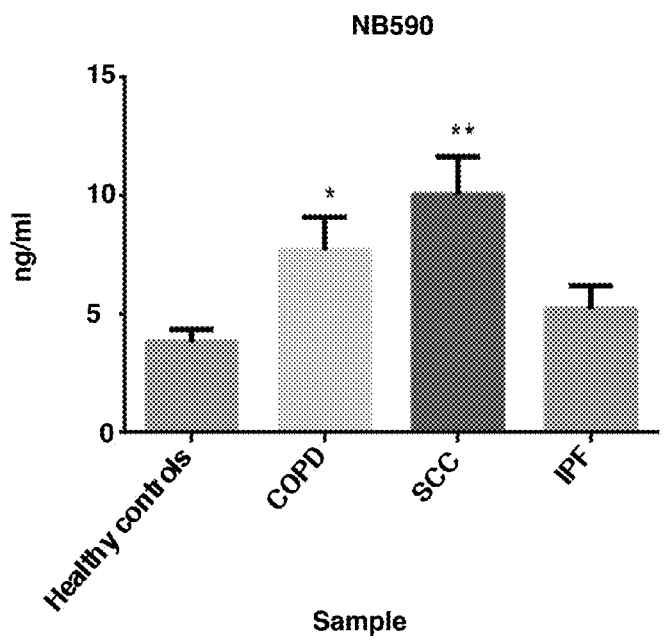
FIG. 3 shows concentrations of the NB590 free peptides in serum from COPD, IPF and squamous cell carcinoma (SCC) of patients as well as controls obtained in Example 3. * denotes a p-value≤0.05 and ** denotes a p-value≤0.05. The standard error of the mean is also shown.

Finally, the NB590 antibody was tested in serum samples from patients with COPD, IPF or squamous cell carcinoma and compared to healthy controls (FIG. 3). There is a significant difference in the concentration of the NB590 fragments in COPD and squamous cell carcinoma patients compared to the healthy controls. Although a tendency for higher levels was observed, there was no statistically significant difference between controls and patients with IPF. This might be explained by the fact that this was a cross-sectional study whereas a longitudinal study of IPF patients may show a more significant difference.

EXAMPLE 4 MONOCLONAL ANTIBODY NB592

Figure 4:
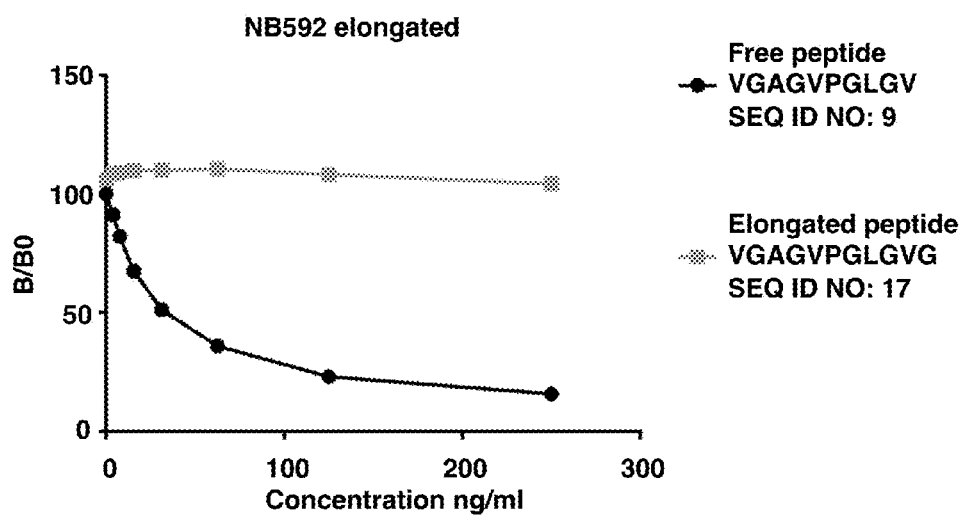
FIG. 4 shows results obtained in Example 4 of an ELISA and shows a measured B/B$_0$ ratio compared to the concentration of free peptide SEQ ID NO:9) and elongated peptide (NB592) (VGAGVPGLGVG, SEQ ID NO:17) after incubation with NB592 monoclonal antibody. There is almost no reactivity towards the elongated peptide.

FIG. 4 shows the reactivity of the free and elongated peptide towards the NB592 antibody. A decrease in absorbance is seen together with an increase in free peptide concentration. This is due an increased reaction with the free peptide instead of the screening peptide in the wells. This was not the case for the elongated peptide as the stable $B/B_0$ levels indicated a very low or no reaction between the elongated peptide and the NB592 antibody.

Figure 5:
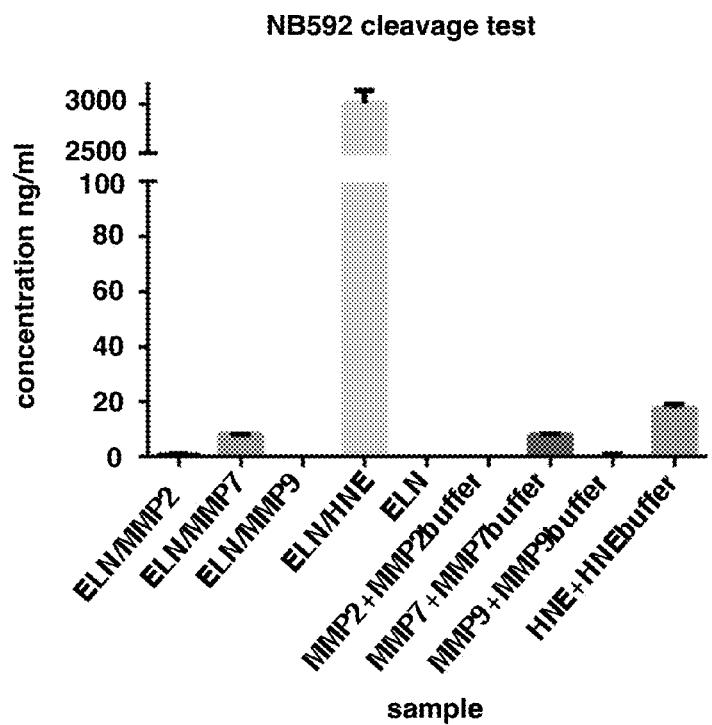
FIG. 5 shows results characterising the NB592 monoclonal antibody obtained in Example 4.

Subsequently, the reactivity of the NB592 antibody was tested towards elastin, elastin cleaved in vitro with MMP2, MMP7, MMP9 and HNE and the proteases in their respective buffers (FIG. 5). The reactivity of the selected proteases in their buffers only, is also included. The NB592 monoclonal antibody clearly measures the elastin fragments derived by HNE. Free peptide concentrations were applied as reference. The NB592 antibody has a very high reactivity towards elastin cleaved with HNE. The reactivity of the NB592 antibody and intact elastin or elastin cleaved with other proteases is close to the lower limit of detection of the assay. A minor signal is shown for the HNE and its buffer alone but the signal is over 100 times smaller than the signal for elastin cleaved with HNE.

Finally, the NB592 antibody was tested in serum samples from patients with COPD, IPF or squamous cell carcinoma and compared to healthy controls (FIG. 6). Although there was a high tendency for increases in levels there were no significant differences (p<0.05) in the concentration of the NB592 fragments in COPD and squamous cell carcinoma patients compared to the healthy controls. There was no difference between controls and patients with IPF. This might be explained by the fact that this was a cross-sectional study whereas a longitudinal study of IPF patients may show a difference.

EXAMPLE 5 (COMPARATIVE) MONOCLONAL ANTIBODY NB593

FIG. 7 shows the reactivity of the free and elongated peptide towards the NB593 antibody. A decrease in absorbance is seen together with an increase in free peptide concentration. This is due an increased reaction with the free peptide instead of the screening peptide in the wells. This was not the case for the elongated peptide as the stable $B/B_0$ levels indicated a very low or no reaction between the NB593 antibody.

Subsequently, the reactivity of the NB593 antibody was tested towards elastin, elastin cleaved in vitro with HNE and the HNE buffer. The 593 monoclonal antibody clearly has a very high reactivity towards elastin fragments derived by HNE compared to the intact elastin and measures such fragments. Free peptide concentrations were applied as reference. The reactivity of the NB593 antibody towards intact elastin or the HNE buffer is very low.

And finally, FIG. 9 shows the reactivity of the NB593 antibody and human serum samples from COPD patients and healthy controls. The data shows that the fragment recognised by antibody NB593 is absent, or only present in undetectable amounts, in the serum of healthy controls and diseased.

EXAMPLE 6 (COMPARATIVE) MONOCLONAL ANTIBODY NB 595

FIG. 10 shows the reactivity of the free and elongated peptide towards the NB595 antibody. A decrease in absorbance is seen together with an increase in free peptide concentration. This is due to an increased reaction with the free peptide instead of the screening peptide in the wells. This was not the case for the elongated peptide as the stable $B/B_0$ levels indicated a very low or no reaction with the NB595 antibody.

Subsequently (FIG. 11), the reactivity of the NB595 antibody was tested towards elastin, elastin cleaved in vitro with MMP2, MMP7, MMP9 and HNE and the proteases in their respective buffers. The 595 monoclonal antibody clearly measures the elastin fragments derived by MMP7 and has a high reactivity towards elastin cleaved with MMP7. Free peptide concentrations were applied as reference. The reactivity of the NB595 antibody towards intact elastin or elastin cleaved with other proteases is close to the lower limit of detection of the assay.

Finally, FIG. 12 shows the reactivity of the NB595 antibodies and pooled human serum samples from COPD patients and healthy controls. The data show that the NB595 fragment is not elevated in COPD patients. There is therefore limited biological relevance for this antibody.

EXAMPLE 7 NB599

FIG. 13 shows the reactivity of the free and elongated peptide towards the NB599 antibody. A decrease in absorbance is seen together with an increase in free peptide concentration. This is due an increased reaction with the free peptide instead of the screening peptide in the wells. The decrease in absorbance was significantly lower for elongated peptide as the $B/B_0$ levels indicated weak reactions between the peptide and the NB599 antibody.

Subsequently, the reactivity of the NB599 antibody towards elastin, elastin cleaved in vitro with MMP2, MMP7, MMP9 and HNE and the proteases in their respective buffers (FIG. 14) was determined. The NB599 monoclonal antibody clearly measures the elastin fragments derived by MMP7. The NB599 antibody has a much higher reactivity towards elastin cleaved with MMP7 than elastin cleaved with other proteases. There is some reactivity towards the HNE+HNE buffer but this is still much lower than elastin cleaved with HNE.

And finally, the presence of Elastin fragments was tested in serum samples from patients with COPD, IPF or squamous cell carcinoma and compared to healthy controls (FIG. 15) using the NB599 test. There is a significant difference in the concentration of the NB599 fragments in COPD, IPF and squamous cell carcinoma patients compared to the healthy controls. Especially the squamous cell carcinoma and COPD patients had increased levels of the NB599 elastin fragment.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

Barroso, B., Abello, N., & Bischoff, R. 2006, "Study of human lung elastin degradation by different elastases using high-performance liquid chromatography/mass spectrometry", Anal. Biochem., vol. 358, no. 2, pp. 216-224.

Carter, R. I., Mumford, R. A., Treonze, K. M., Finke, P. E., Davies, P., Si, Q., Humes, J. L., Dirksen, A., Piitulainen, E., Ahmad, A., & Stockley, R. A. 2011, "The fibrinogen cleavage product Aalpha-Val360, a specific marker of neutrophil elastase activity in vivo", Thorax, vol. 66, no. 8, pp. 686-691.

Carter, R. I., Ungurs, M. J., Mumford, R. A., & Stockley, R. A. 2013, "Aalpha-Val360: a marker of neutrophil elastase and COPD disease activity", Eur. Respir. J., vol. 41, no. 1, pp. 31-38.

Finlay, G. A., O'Driscoll, L. R., Russell, K. J., D'Arcy, E. M., Masterson, J. B., Fitzgerald, M. X., & O'Connor, C. M. 1997, "Matrix metalloproteinase expression and production by alveolar macrophages in emphysema", Am. J. Respir. Crit Care Med., vol. 156, no. 1, pp. 240-247.

Gefter, M. L., Margulies, D. H., & Scharff, M. D. 1977, "A simple method for polyethylene glycol-promoted hybridization of mouse myeloma cells", Somatic. Cell Genet., vol. 3, no. 2, pp. 231-236.

He, J., Turino, G. M., & Lin, Y. Y. 2010, "Characterization of peptide fragments from lung elastin degradation in chronic obstructive pulmonary disease", Exp. Lung Res., vol. 36, no. 9, pp. 548-557.

Heinz, A., Taddese, S., Sippl, W., Neubert, R. H., & Schmelzer, C. E. 2011, "Insights into the degradation of human elastin by matrilysin-1", Biochimie, vol. 93, no. 2, pp. 187-194.

Ma, S., Lin, Y. Y., & Turino, G. M. 2007, "Measurements of desmosine and isodesmosine by mass spectrometry in COPD", Chest, vol. 131, no. 5, pp. 1363-1371.

Maclay, J. D., McAllister, D. A., Rabinovich, R., Haq, I., Maxwell, S., Hartland, S., Connell, M., Murchison, J. T., van Beek, E. J., Gray, R. D., Mills, N. L., & Macnee, W. 2012, "Systemic elastin degradation in chronic obstructive pulmonary disease", Thorax, vol. 67, no. 7, pp. 606-612.

Rosas, I. O., Richards, T. J., Konishi, K., Zhang, Y., Gibson, K., Lokshin, A. E., Lindell, K. O., Cisneros, J., Macdonald, S. D., Pardo, A., Sciurba, F., Dauber, J., Selman, M., Gochuico, B. R., & Kaminski, N. 2008, "MMP1 and MMP7 as potential peripheral blood biomarkers in idiopathic pulmonary fibrosis", PLoS. Med., vol. 5, no. 4, p. e93.

Skjot-Arkil, H., Clausen, R. E., Nguyen, Q. H., Wang, Y., Zheng, Q., Martinez, F. J., Hogaboam, C. M., Han, M., Klickstein, L. B., Larsen, M. R., Nawrocki, A., Leeming, D. J., & Karsdal, M. A. 2012, "Measurement of MMP-9 and -12 degraded elastin (ELM) provides unique information on lung tissue degradation", *BMC. Pulm. Med.*, vol. 12, no. 1, p. 34.

Skjot-Arkil, H., Clausen, R. E., Rasmussen, L. M., Wang, W., Wang, Y., Zheng, Q., Mickley, H., Saaby, L., Diederichsen, A. C., Lambrechtsen, J., Martinez, F. J., Hogaboam, C. M., Han, M., Larsen, M. R., Nawrocki, A., Vainer, B., Krustrup, D., Bjorling-Poulsen, M., Karsdal, M. A., & Leeming, D. J. 2013, "Acute Myocardial Infarction and Pulmonary Diseases Result in Two Different Degradation Profiles of Elastin as Quantified by Two Novel ELISAs", *PLoS. One.*, vol. 8, no. 6, p. e60936.

Starcher, B., O'Neal, P., Granstein, R. D., & Beissert, S. 1996, "Inhibition of neutrophil elastase suppresses the development of skin tumors in hairless mice", *J. Invest Dermatol.*, vol. 107, no. 2, pp. 159-163.

Zhang, J., Jin, X., Fang, S., Wang, R., Li, Y., Wang, N., Guo, W., Wang, Y., Wen, D., Wei, L., Dong, Z., & Kuang, G. 2005, "The functional polymorphism in the matrix metalloproteinase-7 promoter increases susceptibility to esophageal squamous cell carcinoma, gastric cardiac adenocarcinoma and non-small cell lung carcinoma", *Carcinogenesis*, vol. 26, no. 10, pp. 1748-1753.

The invention claimed is:

1. A method of bioassay for the quantification of peptide fragments comprising a neo-epitope formed at a cleavage site by cleavage in vivo of elastin by a proteinase at said site, said method comprising contacting a sample comprising said peptide fragments with an immunological binding partner having specific binding affinity for said neo-epitope and determining the level of binding of said immunological binding partner to peptide fragments in said sample, wherein said immunological binding partner has specific binding affinity for one of the following C-terminal sequences:

```
                                            (SEQ ID NO: 2)
.........FGPGVV||'334

(SEQ ID NO: 3)
.........VPGLGV||'602 or has specific binding affinity for the following
N-terminal sequence:
                                            (SEQ ID NO: 4)
208'||IKAPKL......
``` and wherein the immunological binding partner is not specifically reactive with the sequence . . . FGPGVVG (SEQ ID NO:5) if it is reactive with . . . FGPGVV (SEQ ID NO: 2), and is not specifically reactive with . . . VPGLGVG (SEQ ID NO: 6) if it is reactive with . . . VPGLGV (SEQ ID NO: 3), and is not specifically reactive with PIKAPKL . . . (SEQ ID NO: 7) if it is reactive with IKAPKL . . . (SEQ ID NO: 4).

2. A method as claimed in claim 1, wherein said immunological binding partner is a monoclonal antibody or a fragment of a monoclonal antibody having specific binding affinity.

3. A method as claimed in claim 1, wherein said method is conducted as a competition immunoassay in which said immunological binding partner and a competition agent are incubated in the presence of said sample and the competition agent competes with the peptide fragments in the sample to bind to the immunological binding partner.

4. A method as claimed in claim 3, wherein said competition agent is a synthetic peptide or is a purified native peptide formed by cleavage of elastin so as to reveal said neo-epitope.

5. A method as claimed in claim 1, wherein said method is conducted as a sandwich immunoassay in which said immunological binding partner and a further immunological binding partner having specific binding affinity for a peptide sequence contained in peptide fragments bound by said immunological binding partner are incubated in the presence of said sample and both bind together to said peptide fragments in the sample.

6. A method as claimed in claim 1, wherein the sample is a sample of urine, serum, blood, plasma, or saliva.

7. A method as claimed in claim 1, wherein the sample is a patient derived sample, said method further comprising comparing the determined level of said binding of said peptide fragments with values characteristic of (a) comparable healthy individuals and/or (b) a pathological condition.

* * * * *

SEQUENCE LISTING

```
<160> NUMBER OF SEQ ID NOS: 17

<210> SEQ ID NO 1
<211> LENGTH: 786
<212> TYPE: PRT
<213> ORGANISM: Homo sapiens
<220> FEATURE:
<223> OTHER INFORMATION: Elastin

<400> SEQUENCE: 1

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
        210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
                260                 265                 270
```

-continued

```
Val Leu Pro Gly Val Gly Ala Gly Val Pro Gly Pro Gly Ala
        275                 280                 285

Ile Pro Gly Ile Gly Ile Ala Gly Val Gly Thr Pro Ala Ala
        290                 295                 300

Ala Ala Ala Ala Ala Ala Lys Ala Ala Lys Tyr Gly Ala Ala
305                 310                 315                 320

Gly Leu Val Pro Gly Pro Gly Phe Gly Pro Val Val Gly Val
                325                 330                 335

Pro Gly Ala Gly Val Pro Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
        370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Ala Ala Gly Ala Gly Val Leu Gly Gly Leu Val
        450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Lys Ala Ala Ala Lys
            485                 490                 495

Ala Ala Gln Phe Gly Leu Val Pro Gly Val Gly Val Ala Pro Gly Val
                500                 505                 510

Gly Val Ala Pro Gly Val Gly Val Ala Pro Gly Val Gly Leu Ala Pro
            515                 520                 525

Gly Val Gly Val Ala Pro Gly Val Gly Val Ala Pro Gly Val Gly Val
        530                 535                 540

Ala Pro Gly Ile Gly Pro Gly Val Ala Ala Ala Lys Ser Ala
545                 550                 555                 560

Ala Lys Val Ala Ala Lys Ala Gln Leu Arg Ala Ala Gly Leu Gly
                565                 570                 575

Ala Gly Ile Pro Gly Leu Gly Val Gly Val Gly Val Pro Gly Leu Gly
            580                 585                 590

Val Gly Ala Gly Val Pro Gly Leu Gly Val Gly Ala Gly Val Pro Gly
        595                 600                 605

Phe Gly Ala Gly Ala Asp Glu Gly Val Arg Arg Ser Leu Ser Pro Glu
        610                 615                 620

Leu Arg Glu Gly Asp Pro Ser Ser Ser Gln His Leu Pro Ser Thr Pro
625                 630                 635                 640

Ser Ser Pro Arg Val Pro Gly Ala Leu Ala Ala Lys Ala Ala Lys
                645                 650                 655

Tyr Gly Ala Ala Val Pro Gly Val Leu Gly Gly Leu Gly Ala Leu Gly
        660                 665                 670

Gly Val Gly Ile Pro Gly Gly Val Val Gly Ala Gly Pro Ala Ala Ala
        675                 680                 685
```

```
Ala Ala Ala Ala Lys Ala Ala Lys Ala Ala Gln Phe Gly Leu Val
        690             695             700
Gly Ala Ala Gly Leu Gly Gly Leu Gly Val Gly Leu Gly Val Pro
705             710             715             720
Gly Val Gly Gly Leu Gly Gly Ile Pro Pro Ala Ala Ala Lys Ala
                725             730             735
Ala Lys Tyr Gly Ala Ala Gly Leu Gly Gly Val Leu Gly Ala Gly
            740             745             750
Gln Phe Pro Leu Gly Gly Val Ala Ala Arg Pro Gly Phe Gly Leu Ser
        755             760             765
Pro Ile Phe Pro Gly Gly Ala Cys Leu Gly Lys Ala Cys Gly Arg Lys
770             775             780
Arg Lys
785
```

<210> SEQ ID NO 2
<211> LENGTH: 6
<212> TYPE: PRT
<213> ORGANISM: Homo sapiens
<220> FEATURE:
<223> OTHER INFORMATION: Neo-epitope sequence of elastin cleavage
      fragment

<400> SEQUENCE: 2

Phe Gly Pro Gly Val Val
1               5

<210> SEQ ID NO 3
<211> LENGTH: 6
<212> TYPE: PRT
<213> ORGANISM: Homo sapiens
<220> FEATURE:
<223> OTHER INFORMATION: Neo-epitope sequence of elastin cleavage
      fragment

<400> SEQUENCE: 3

Val Pro Gly Leu Gly Val
1               5

<210> SEQ ID NO 4
<211> LENGTH: 6
<212> TYPE: PRT
<213> ORGANISM: Homo sapiens
<220> FEATURE:
<223> OTHER INFORMATION: Neo-epitope sequence of elastin cleavage
      fragment

<400> SEQUENCE: 4

Ile Lys Ala Pro Lys Leu
1               5

<210> SEQ ID NO 5
<211> LENGTH: 7
<212> TYPE: PRT
<213> ORGANISM: Homo sapiens
<220> FEATURE:
<223> OTHER INFORMATION: Elongated terminal sequence of elastin cleavage
      fragment

<400> SEQUENCE: 5

Phe Gly Pro Gly Val Val Gly
1               5

-continued

```
<210> SEQ ID NO 6
<211> LENGTH: 7
<212> TYPE: PRT
<213> ORGANISM: Homo sapiens
<220> FEATURE:
<223> OTHER INFORMATION: Elongated terminal sequence of elastin cleavage
      fragment

<400> SEQUENCE: 6

Val Pro Gly Leu Gly Val Gly
1               5

<210> SEQ ID NO 7
<211> LENGTH: 7
<212> TYPE: PRT
<213> ORGANISM: Homo sapiens
<220> FEATURE:
<223> OTHER INFORMATION: Elongated terminal sequence of elastin cleavage
      fragment

<400> SEQUENCE: 7

Pro Ile Lys Ala Pro Lys Leu
1               5

<210> SEQ ID NO 8
<211> LENGTH: 10
<212> TYPE: PRT
<213> ORGANISM: Artificial sequence
<220> FEATURE:
<223> OTHER INFORMATION: Immunisation peptide

<400> SEQUENCE: 8

Gly Gly Pro Gly Phe Gly Pro Gly Val Val
1               5                   10

<210> SEQ ID NO 9
<211> LENGTH: 9
<212> TYPE: PRT
<213> ORGANISM: Artificial sequence
<220> FEATURE:
<223> OTHER INFORMATION: Immunisation peptide

<400> SEQUENCE: 9

Gly Ala Gly Val Pro Gly Leu Gly Val
1               5

<210> SEQ ID NO 10
<211> LENGTH: 10
<212> TYPE: PRT
<213> ORGANISM: Artificial sequence
<220> FEATURE:
<223> OTHER INFORMATION: Immunisation peptide

<400> SEQUENCE: 10

Ile Lys Ala Pro Lys Leu Pro Gly Gly Tyr
1               5                   10

<210> SEQ ID NO 11
<211> LENGTH: 9
<212> TYPE: PRT
<213> ORGANISM: Artificial sequence
<220> FEATURE:
<223> OTHER INFORMATION: Immunisation peptide

<400> SEQUENCE: 11

Gly Leu Gly Gly Val Leu Gly Gly Ala
1               5
```

```
<210> SEQ ID NO 12
<211> LENGTH: 10
<212> TYPE: PRT
<213> ORGANISM: Artificial sequence
<220> FEATURE:
<223> OTHER INFORMATION: Immunisation peptide

<400> SEQUENCE: 12

Val Phe Tyr Pro Gly Ala Gly Leu Gly Ala
1               5                   10

<210> SEQ ID NO 13
<211> LENGTH: 10
<212> TYPE: PRT
<213> ORGANISM: Artificial sequence
<220> FEATURE:
<223> OTHER INFORMATION: Elongated immunisation peptide

<400> SEQUENCE: 13

Ala Gly Leu Gly Gly Val Leu Gly Gly Ala
1               5                   10

<210> SEQ ID NO 14
<211> LENGTH: 11
<212> TYPE: PRT
<213> ORGANISM: Artificial sequence
<220> FEATURE:
<223> OTHER INFORMATION: Elongated immunisation peptide

<400> SEQUENCE: 14

Gly Val Phe Tyr Pro Gly Ala Gly Leu Gly Ala
1               5                   10

<210> SEQ ID NO 15
<211> LENGTH: 11
<212> TYPE: PRT
<213> ORGANISM: Artificial sequence
<220> FEATURE:
<223> OTHER INFORMATION: Elongated immunisation peptide

<400> SEQUENCE: 15

Pro Ile Lys Ala Pro Lys Leu Pro Gly Gly Tyr
1               5                   10

<210> SEQ ID NO 16
<211> LENGTH: 11
<212> TYPE: PRT
<213> ORGANISM: Artificial sequence
<220> FEATURE:
<223> OTHER INFORMATION: Elongated immunisation peptide

<400> SEQUENCE: 16

Gly Gly Pro Gly Phe Gly Pro Gly Val Val Gly
1               5                   10

<210> SEQ ID NO 17
<211> LENGTH: 10
<212> TYPE: PRT
<213> ORGANISM: Artificial sequence
<220> FEATURE:
<223> OTHER INFORMATION: Elongated immunisation peptide

<400> SEQUENCE: 17

Gly Ala Gly Val Pro Gly Leu Gly Val Gly
1               5                   10
```